(12) United States Patent
Giroir et al.

(10) Patent No.: US 7,445,886 B2
(45) Date of Patent: Nov. 4, 2008

(54) MACROPHAGE MIGRATION INHIBITORY FACTOR AS A MARKER FOR CARDIOVASCULAR RISK

(75) Inventors: Brett P. Giroir, Dallas, TX (US); Monty S. Willis, Dallas, TX (US); Timothy S. Church, Dallas, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 852 days.

(21) Appl. No.: 10/660,301

(22) Filed: Sep. 10, 2003

(65) Prior Publication Data

US 2005/0054117 A1 Mar. 10, 2005

(51) Int. Cl.
*G01N 33/53* (2006.01)
*C12Q 1/00* (2006.01)
*C07K 1/00* (2006.01)

(52) U.S. Cl. .......................................... 435/4; 435/7.1
(58) Field of Classification Search ........................ None
See application file for complete search history.

(56) References Cited

OTHER PUBLICATIONS

Yabunaka et al., Diabetes Care, Feb. 2000, vol. 23, pp.256-258.*
Pan et al. J Vasc Surg 2003. 37:628-635.*
Church et al. International Journal of Obesity 2005. 29:675-681.*
van Dielen et al. The Journal of Clinical Endocrinology & Metabolism 2004. 89(8):4062-4068.*
Garner et al. Am. J. Heart Circ. Physil. 2003. 285:H2500-H2509.*
Kurl et al. Stroke Sep. 2001;32(9):2036-41. Abstract only.*
St-Pierre et al. Am. J. Cardiol. Mar. 1, 2003;91(5):55-8. Abstract only.*

* cited by examiner

*Primary Examiner*—Maher M. Haddad
*Assistant Examiner*—Chun Dahle
(74) *Attorney, Agent, or Firm*—Richard Aron Osman

(57) ABSTRACT

Macrophage migration inhibitory factor (MIF) is a clinically useful biochemical marker of cardiovascular risk. Risk assessment includes the step of detecting in the blood of a person MIF concentration as a marker of cardiovascular risk for the person. The method may further comprise the step of assigning to the person a cardiovascular risk metric proportional to the MIF concentration, and/or prescribing for the person a cardiovascular treatment modality in accordance with the MIF concentration. The method is useful as a primary screen, and may be used in conjunction with or as a substitute for additional tests, such as a stress test, CRP assay, LDL assay, etc. The detecting step may be repeated over time intervals and/or treatment to monitor change in cardiovascular risk for the person over time and/or treatment.

15 Claims, No Drawings ns, et al. Am J Cardiol. 2003 92,10i-8i.
MACROPHAGE MIGRATION INHIBITORY FACTOR AS A MARKER FOR CARDIOVASCULAR RISK

FIELD OF THE INVENTION

The field of the invention is the use of macrophage migration inhibitory factor (MIF) as a marker for cardiovascular risk.

BACKGROUND OF THE INVENTION

Well-known indicia of cardiovascular risk include age, sex, smoking, systolic blood pressure and total cholesterol. In addition, several biochemical markers of cardiovascular health risk have been proposed, including C-reactive protein (CRP; Schishehbor et al., Cleve Clin J. Med. 2003 70, 634-40), B-type natriuretic peptide (BNP; Silver et al., Congest Heart Fail 2003 9,127-32), sialic acid (Crook et al., 1998 Clin Sci 95, 53-57), etc. For a review of several biochemical markers in the management of coronary artery disease, see Rosenson, et al. Am J Cardiol. 2003 92,10i-8i.

Macrophage migration inhibitory factor (MIF) is a pleiotropic cytokine/hormone that has been associated with a number of disease states. MIF expression has been suggested to correlate with diseases like sepsis (Lehmann et al., 2001 Intensive Care Med 27,1412-5), prostate cancer (Meyer-Siegler et al., 2002 Cancer 94, 1449-56; Hudson et al., U.S. Pat. No. 6,043,044), aneurysmal expansion (Pan et al., 2003 J Vasc Surg 37, 628-35), acute myocardial infarction (Yu et al., 2001 Am J Card 88, 774-7), atherosclerosis (Burger-Kentischer, 2002 Circulation 105, 1561-66), diabetes (Sakaue et al., 1999 Mol Med. 5, 361-71), etc., and bypass surgery (Gando et al., 2000 Surg Today 30, 689-94). For a review of pathophysiological aspects of macrophage migration inhibitory factor, see Nishihira, 1998 Int J Mol Med. 2, 17-28.

We have determined that the serum level of MIF is extremely elevated in patients with high cardiovascular risk, and that it falls rapidly when interventions are made which reduce this risk. Prior to our work, MIF levels have never been associated with cardiovascular risk in non-diseased or non-diagnosed persons. Like CRP, MIF is a marker of cardiovascular risk providing clinically important prognostic information in the assessment of overall cardiovascular risk.

SUMMARY OF THE INVENTION

The disclosed methods and kits use serum MIF levels as a marker for morbidity, particularly cardiovascular disease. We found that serum MIF is elevated in adults with high cardiovascular risk and that serum MIF falls with reductions in cardiovascular risk. Our data indicate that MIF has a much greater elevation at onset, tracks better with anticipated health risk, and is not altered by co-therapies, as compared with CRP. For example, hormonal supplements commonly prescribed for post-menopausal women are known to falsely elevate CRP. Hence, MIF is a more accurate marker of overall mortality risk, particularly of cardiovascular risk. The invention provides methods and kits for determining cardiovascular risk in a person not predetermined to be subject to cardiovascular disease. The methods generally comprise the step of detecting MIF concentration in the blood, urine or saliva of the person as a marker of cardiovascular risk for the person.

The method may further comprise the step of assigning to the person a cardiovascular risk metric proportional to the MIF concentration, and/or prescribing for the person a cardiovascular treatment modality in accordance with the MIF concentration.

The method is useful as a primary screen, and may be used in conjunction with or as a substitute for additional assessments of risk, such as a stress test, CRP assay, low-density lipoprotein (LDL) assay, etc.

In particular embodiments, the detecting step is repeated over time intervals and/or treatment to monitor change in cardiovascular risk for the person over time and/or treatment.

DESCRIPTION OF PARTICULAR EMBODIMENTS OF THE INVENTION

We have found that elevated levels of MIF in apparently healthy persons are predictive of future cardiovascular disorders, particularly disorders associated with atherosclerosis. Preferred subject persons are apparently healthy but statistically or professionally determined overweight or obese persons, and/or are subject to or predisposed to type II diabetes. In addition, the likelihood that certain persons will benefit to a greater or a lesser extent from the use of certain therapeutic agents for reducing the risk of a future cardiovascular disorder can be in part determined from the person's MIF level. The predictive value of MIF is independent of other predictors and, for example, is additive with other known cardiovascular risk factors, including various prognostic markers of heart disease, such as CRP, serum amyloid A, interleukin-6, homocysteine, total cholesterol, LDL, apolipoprotein B-100, high-density lipoprotein (HDL), and ratio of total cholesterol to HDL, etc. Protocols for using these other markers, including detecting and monitoring methods, are well-known in the art, and this invention generally provides such protocols using MIF as an alternative marker.

The subject cardiovascular disorders include myocardial infarction, stroke, angina pectoris and peripheral arteriovascular disease. Apparently healthy individuals have not previously had an acute adverse cardiovascular event such as a myocardial infarction (i.e., individuals who are not at an elevated risk of a second adverse cardiovascular event due to a primary adverse cardiovascular event), and generally do not otherwise exhibit symptoms of disease, particularly acute disease.

The invention provides methods for characterizing an apparently healthy individual's risk of, and/or developing their risk profile for developing a future subject cardiovascular disorder. The method comprises obtaining a level of MIF in the individual, typically expressed as MIF concentration, and comparing the level of the marker to a predetermined value. The individual's risk or risk profile of developing a future subject cardiovascular disorder then is characterized based upon the level of the marker in comparison to the predetermined value.

In a particular embodiment, the invention provides a method for evaluating the likelihood that an individual will benefit from treatment with an agent for reducing the risk of a cardiovascular disorder. The agent can be selected from anti-inflammatory agents, anti-thrombotic agents, anti-platelet agents, fibrinolytic agents, lipid reducing agents, direct thrombin inhibitors, and glycoprotein II b/IIIa receptor inhibitors. A preferred agent is aspirin. The individual's MIF level is obtained and compared to a predetermined value, wherein the level of MIF in comparison to the predetermined value is indicative of the likelihood that the individual will benefit from treatment with the agent.

MIF levels can be obtained by any art recognized method. Typically, the level is determined by measuring the level of the marker in body fluid, such as blood, saliva or urine. The level can be determined by immunoassay or other techniques for determining the presence of the marker. A commercial human MIF ELISA detection kit is available from Chemicon (Temecula, Calif.), now Serologicals Corp. (Atlanta, Ga.). Automated analyzers on which tests for MIF can be performed include Dade Behring BN II Plasma Protein System (Dade Behring, Incorporated, Deerfield, Ill., USA), Abbott Laboratories IMx Immunoassay Analyzer (Abbott Laboratories, Abbott Park, Ill., USA), IMMULITE (Diagnostics Products Corporation, Los Angeles, Calif., USA), and IMMAGE (Beckman Coulter, Inc., Fullerton, Calif., USA). The Dade Behring BN II assay utilizes a monoclonal antibody on a polystyrene particle with fixed-time nephelometric measurements. The Abbott IMx assay is a two-site chemiluminescent enzyme immunometric assay with one monoclonal and one polyclonal anti-MIF antibody. The Beckman Coulter IMMAGE assay uses a polyclonal anti-MIF antibody on latex particles with rate nephelometric measurements.

The predetermined value will depend upon the characteristics of the patient, and/or the relevant patient population. The predetermined value can be a single value, multiple values, a single range or multiple ranges. Thus, in one embodiment, the predetermined value is a plurality of predetermined marker level ranges, and the comparing step comprises determining in which of the predetermined marker level ranges the individual's level falls. In another embodiment, the predetermined value is a historical value from the patient.

The invention is adapted to determining which individuals will preferentially benefit from treatment with an agent for reducing the risk in the individuals of a cardiovascular disorder, and facilitates selection of candidate populations for clinical trials and for treatment with candidate drugs, by identifying, for example, the individuals most likely to benefit from a given treatment.

The invention also involves a method for treating subjects, with anti-inflammatory therapies, to reduce the likelihood of subsequent cardiovascular disorders. An anti-inflammatory agent is administered to a subject who has an above-normal level of MIF, but who is preferably otherwise free of symptoms indicating use of an anti-inflammatory agent. Preferred subjects are apparently healthy subjects free of current need for anti-inflammatory treatment, such as free of symptoms of rheumatoid arthritis, chronic back pain, autoimmune diseases, and the like.

The invention also provides kits specifically tailored to practicing the subject method. In one embodiment, the kits comprise materials for assaying MIF blood concentration and an associated instructional medium describing a subject method.

EXAMPLES

I. Comparison of MIF and CRP levels as correlates to reductions in cardiovascular risk. This study was designed to compare MIF and CRP as markers correlating with cardiovascular risk.

Methods: In an initial demonstration, we monitored MIF in obese adults, with very high cardiovascular risk, who were subjected to a one-year regimen of diet and exercise.

Results: We found that MIF levels tracked progress (reduction in cardiovascular risk) through the treatment regimen better than did CRP. In our control group (n=83), MIF levels were 38+/−16 ng/ml. The obese patients at baseline are elevated to 100+ng/ml generally and drop to normal levels generally after 1 year.

Conclusion: Our data indicate that MIF has a much greater elevation at onset, tracks better with anticipated health risk, and is not altered by co-therapies, as compared with CRP.

II. Comparison of MIF levels and the calculated Framingham Coronary Heart Disease Risk Score (FCRS). This study was designed to evaluate the relationship between MIF levels and the FCRS. Our study protocol was adapted from Albert et al, Circulation. 2003, 108, 161-5.

Methods: MIF concentrations in blood plasma are compared with calculated 10-year FCRS in a cross-sectional survey of 1600 individuals free of apparent cardiovascular disease.

Results: Among men and women, MIF levels are significantly related to 10-year Framingham Coronary Heart Disease Risk categories [total cholesterol (TC) score for men and women: r=0.29 and r=0.22, respectively; LDL cholesterol score for men and women: r=0.29 and r=0.22, respectively, all probability values<0.01].

Conclusion: This study demonstrates that MIF levels significantly correlate with calculated 10-year Framingham Coronary Heart Disease Risk in both men and women.

III. Comparison of MIF and LDL cholesterol levels in the prediction of first cardiovascular events. This study was designed to compare MIF and LDL cholesterol levels as predictors of first cardiovascular events. Our study protocol was adapted from Ridker et al., 2002, N Engl J. Med.347, 1557-65.

Methods: MIF and LDL cholesterol are measured at base line in apparently healthy American women, who are then followed for a mean of eight years for the occurrence of myocardial infarction, ischemic stroke, coronary revascularization, or death from cardiovascular causes. We then assess the value of these two measurements in predicting the risk of cardiovascular events in the study population.

Results: Base-line levels of MIF and LDL cholesterol have a strong linear relation with the incidence of cardiovascular events. After adjustment for age, smoking status, the presence or absence of diabetes mellitus, categorical levels of blood pressure, and use or nonuse of hormone-replacement therapy, the relative risks of first cardiovascular events according to increasing quintiles of MIF, as compared with the women in the lowest quintile, are 1.4, 1.6, 2.0, and 2.3 (P<0.001), whereas the corresponding relative risks in increasing quintiles of LDL cholesterol, as compared with the lowest, are 0.9, 1.1, 1.3, and 1.5 (P<0.001). Similar effects are observed in separate analyses of each component of the composite end point and among users and nonusers of hormone-replacement therapy. Overall, 77 percent of all events occur among women with LDL cholesterol levels below 160 mg per deciliter (4.14 mmol per liter), and 46 percent occur among those with LDL cholesterol levels below 130 mg per deciliter (3.36 mmol per liter). By contrast, because MIF and LDL cholesterol measurements tend to identify different high-risk groups, screening for both biologic markers provides better prognostic information than screening for either alone. Independent effects are also observed for MIF in analyses adjusted for all components of the Framingham risk score.

Conclusion: Our data indicate that MIF level is a stronger predictor of cardiovascular events than the LDL cholesterol level and that it adds prognostic information to that conveyed by the Framingham risk score.

The foregoing descriptions of particular embodiments and examples are offered by way of illustration and not by way of limitation. Unless contraindicated or noted otherwise, in these descriptions and throughout this specification, the terms "a" and "an" mean one or more, the term "or" means and/or.

All publications and patent applications cited in this specification and all references cited therein are herein incorporated by reference as if each individual publication or patent application or reference were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of determining cardiovascular risk in a person without cardiovascular disease or without a diagnosis thereof, the method comprising the step of:
   determining a test MIF concentration in the blood, saliva or urine of the person as a marker of cardiovascular risk for the person, wherein an elevated test MIF concentration compared with a control MIF concentration indicates that the person is subject to elevated cardiovascular risk, and a further step selected from the group consisting of: (a) assigning to the person a cardiovascular risk metric in accordance with the test MIF concentration; (b) prescribing for the person a cardiovascular treatment modality in accordance with the test MIF concentration; and (c) making an additional assessment of cardiovascular risk of the person in accordance with the test MIF concentration, the additional assessment selected from the group consisting of a stress test, a CRP assay and an LDL assay.

2. The method of claim 1, wherein the further step comprises assigning to the person a cardiovascular risk metric in accordance with the test MIF concentration.

3. The method of claim 1, wherein the further step comprises prescribing for the person a cardiovascular treatment modality in accordance with the test MIF concentration.

4. The method of claim 1, wherein the further step comprises making an additional assessment of cardiovascular risk of the person in accordance with the test MIF concentration, the additional assessment selected from the group consisting of a stress test, a CRP assay and an LDL assay.

5. The method of claim 1, wherein the determining step is repeated over time intervals to monitor change in cardiovascular risk for the person over time.

6. The method of claim 1, wherein the determining step is repeated over treatment to monitor change in cardiovascular risk for the person over treatment.

7. A method for characterizing a risk of developing a future cardiovascular disorder in an individual, the method comprising steps:
   obtaining a test MIF level in the blood, saliva or urine of the individual,
   comparing the test MIF level to a predetermined control MIF value, and
   characterizing the individual's risk of developing the future cardiovascular disorder based upon the test MIF level in comparison to the predetermined control MIF value.

8. The method of claim 7, wherein the predetermined control MIF value is a plurality of predetermined MIF level ranges and the comparing step comprises determining in which of the predetermined MIF level ranges the individual's test MIF level falls.

9. The method of claim 7, wherein the individual is statistically overweight or obese.

10. The method of claim 7, wherein the cardiovascular disorder is selected from the group consisting of stroke and myocardial infarction.

11. A method for evaluating the likelihood that an individual will benefit from treatment with an agent for reducing the risk of a cardiovascular disorder, the method comprising steps:
    obtaining a test MIF level in the blood, saliva or urine of the individual, and
    comparing the test MIF level to a predetermined control MIF value,
    wherein the test MIF level in comparison to the predetermined control MIF value is indicative of whether the individual will benefit from treatment with said agent.

12. The method of claim 11, wherein the predetermined control MIF value is a plurality of predetermined MIF concentration ranges and the comparing step comprises determining in which of the predetermined MIF concentration ranges the individual's test MIF level falls.

13. The method of claim 11, wherein the individual is statistically overweight or obese.

14. The method of claim 11, wherein the cardiovascular disorder is selected from the group consisting of stroke and myocardial infarction.

15. The method of claim 11, wherein the agent is aspirin.

* * * * *